United States Patent
Agnew

(10) Patent No.: US 8,043,352 B2
(45) Date of Patent: Oct. 25, 2011

(54) MEDICAL DEVICE DELIVERY SYSTEM WITH CAPTIVE INNER MEMBER

(75) Inventor: Charles W. Agnew, West Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1277 days.

(21) Appl. No.: 11/420,036

(22) Filed: May 24, 2006

(65) Prior Publication Data

US 2006/0271064 A1 Nov. 30, 2006

Related U.S. Application Data

(60) Provisional application No. 60/684,042, filed on May 24, 2005.

(51) Int. Cl.
*A61F 2/06* (2006.01)
(52) U.S. Cl. ...................................................... 623/1.11
(58) Field of Classification Search .................. 623/1.11, 623/1.23, 1.12; 606/108
See application file for complete search history.

(56) References Cited

U.S. PATENT DOCUMENTS

| | | | |
|---|---|---|---|
| 4,762,129 A | 8/1988 | Bonzel | |
| 5,626,603 A * | 5/1997 | Venturelli et al. | 623/1.11 |
| 5,989,263 A * | 11/1999 | Shmulewitz | 606/108 |
| 6,200,336 B1 | 3/2001 | Pavcnik et al. | |
| 6,616,680 B1 | 9/2003 | Thielen | |
| 2003/0018293 A1 * | 1/2003 | Tanghoj et al. | 604/19 |
| 2003/0212431 A1 | 11/2003 | Brady et al. | |
| 2004/0039345 A1 * | 2/2004 | Benz et al. | 604/227 |
| 2004/0064067 A1 | 4/2004 | Ward | |
| 2004/0073230 A1 | 4/2004 | Mulholland et al. | |
| 2004/0167566 A1 | 8/2004 | Beulke et al. | |
| 2004/0186558 A1 | 9/2004 | Pavcnik et al. | |
| 2004/0260389 A1 | 12/2004 | Case et al. | |
| 2005/0165354 A1 * | 7/2005 | Schwartz et al. | 604/152 |
| 2006/0282157 A1 | 12/2006 | Hill et al. | |
| 2007/0067021 A1 | 3/2007 | Haverkost et al. | |
| 2007/0129788 A1 | 6/2007 | Drasler et al. | |

FOREIGN PATENT DOCUMENTS

EP 1179321 A2 2/2002

OTHER PUBLICATIONS 8 pages—Schneider (Eur.) AG v. Scimed Life Sys., 852 F. Supp. 813 (D. Minn. 1994).

* cited by examiner

*Primary Examiner* — Gary Jackson
*Assistant Examiner* — Katherine Dowe
(74) *Attorney, Agent, or Firm* — Buchanan Nipper

(57) ABSTRACT

Delivery systems for delivering and deploying expandable intraluminal medical devices at a desired point of treatment within a body vessel are provided. The delivery systems comprise a sheath member and an inner member slideably disposed within a cavity formed by the sheath member. An expandable intraluminal medical device is disposed about the inner member and is initially positioned within the delivery system. A means for preventing axial movement of the inner member holds the inner member in position so that, while the delivery system and medical device are positioned at a desired point of treatment, the sheath member can be retracted while an axial position of the inner member is substantially maintained.

18 Claims, 3 Drawing Sheets

MEDICAL DEVICE DELIVERY SYSTEM WITH CAPTIVE INNER MEMBER

CROSS-REFERENCE TO RELATED APPLICATION

The present application claims priority to the provisional patent application identified by U.S. Ser. No. 60/684,042, filed on May 24, 2005, the entire content of which is hereby expressly incorporated herein by reference.

FIELD

The invention relates to delivery systems for placement of self-expandable intraluminal medical devices within a body vessel.

BACKGROUND

Minimally invasive medicine, the practice of gaining access to a body vessel, duct, or organ using a guiding member to facilitate the subsequent introduction of other medical devices, has been evolving since the Seldinger technique was first popularized during the 1950's and 1960's. Self-expandable intraluminal medical devices are frequently used in a variety of minimally invasive procedures. For example, self-expandable stents are used to provide support to various vessels and ducts in the circulatory and the gastrointestinal systems. Also, prosthetic valves are gaining popularity as tools for supplementing and/or replacing natural valves in a variety of locations within the body, such as veins and the heart and its associated vessels.

When placing medical devices within a body vessel, it is desirable to place a medical device as close to the desired point of treatment as possible. There are delivery systems known in the art that utilize a pushing function to move a medical device from the system to a position within a body vessel at a point of treatment. This method of delivery requires the delivery system operator to estimate the point at which a device will be deployed. Further, the operator is required to position the system appropriately in the body vessel to deliver the medical device as near as possible to the point of treatment.

There is a need for delivery systems that offer more accurate delivery of medical devices near the desired point of treatment, especially delivery systems adapted for placement of self-expandable intraluminal medical devices.

SUMMARY OF EXEMPLARY EMBODIMENTS

The invention provides medical device delivery systems. A delivery system according to one exemplary embodiment comprises a sheath member defining a first passageway, an inner member slidably disposed within a distal cavity of the first passageway, a fluid that substantially prevents movement of the inner member within the distal cavity, and a groove on the first inner surface of the sheath member. The groove prevents the inner member from completely exiting the sheath member as the sheath member is retracted. A self-expandable intraluminal medical device is disposed on a mounting region of the inner member the sheath member has an exchange port defined by a circumferential wall.

In another exemplary embodiment, a pusher is used rather than a fluid. The pusher can be used to provide resistance against movement of the inner member within the distal cavity.

Additional understanding of the invention can be obtained with review of the detailed description of exemplary embodiments, below, and the appended drawings illustrating exemplary embodiments.

DETAILED DESCRIPTION OF EXEMPLARY EMBODIMENTS

The following detailed description and the appended drawings describe and illustrate exemplary embodiments of the invention for purposes of enabling one of ordinary skill in the relevant art to make and use the invention. The description and drawings are not intended to limit the scope of the invention, or its protection, in any manner.

Figure 1:
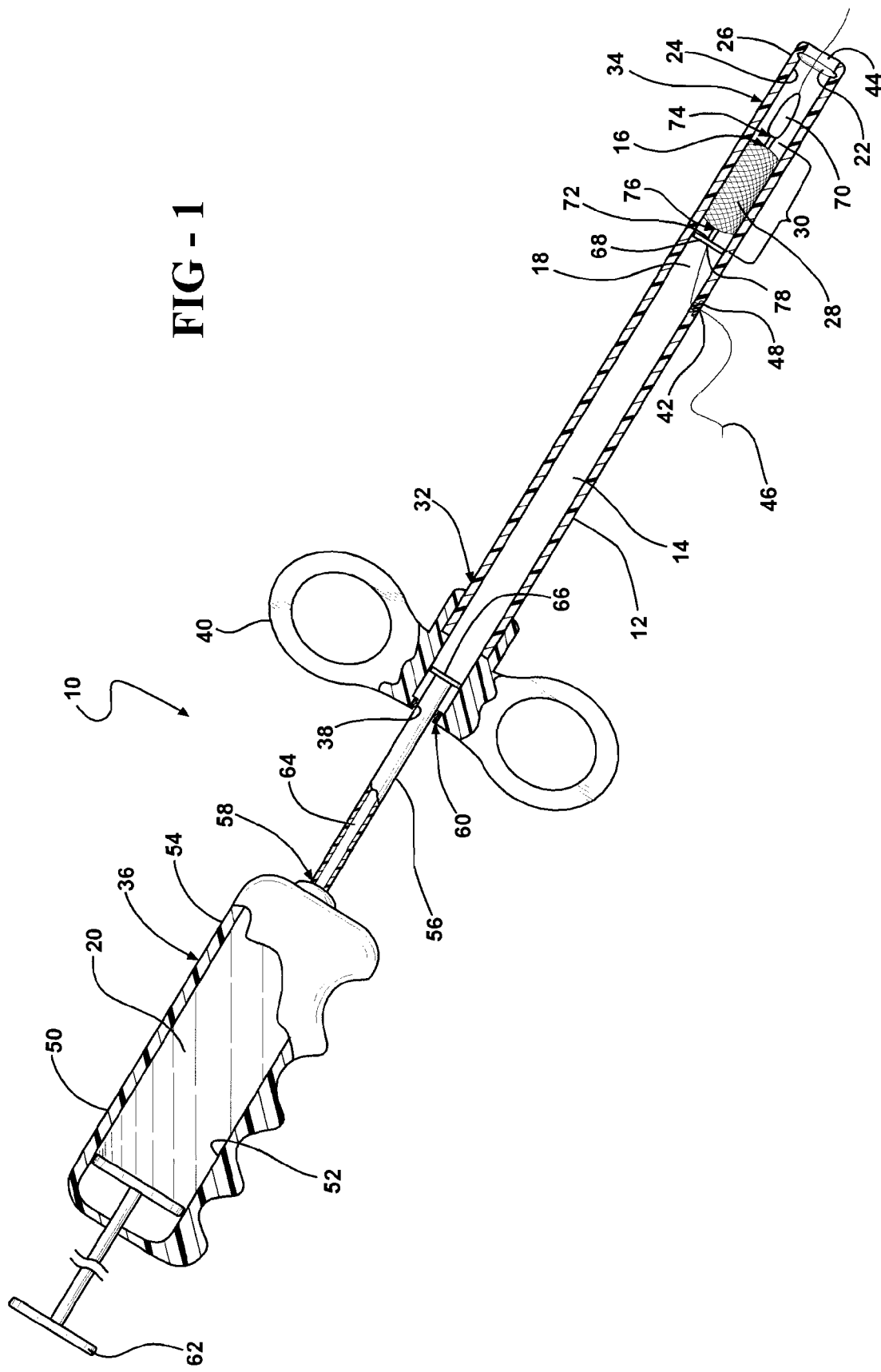
FIG. 1 is a sectional view of a delivery system according to a first exemplary embodiment.
Figure 2:
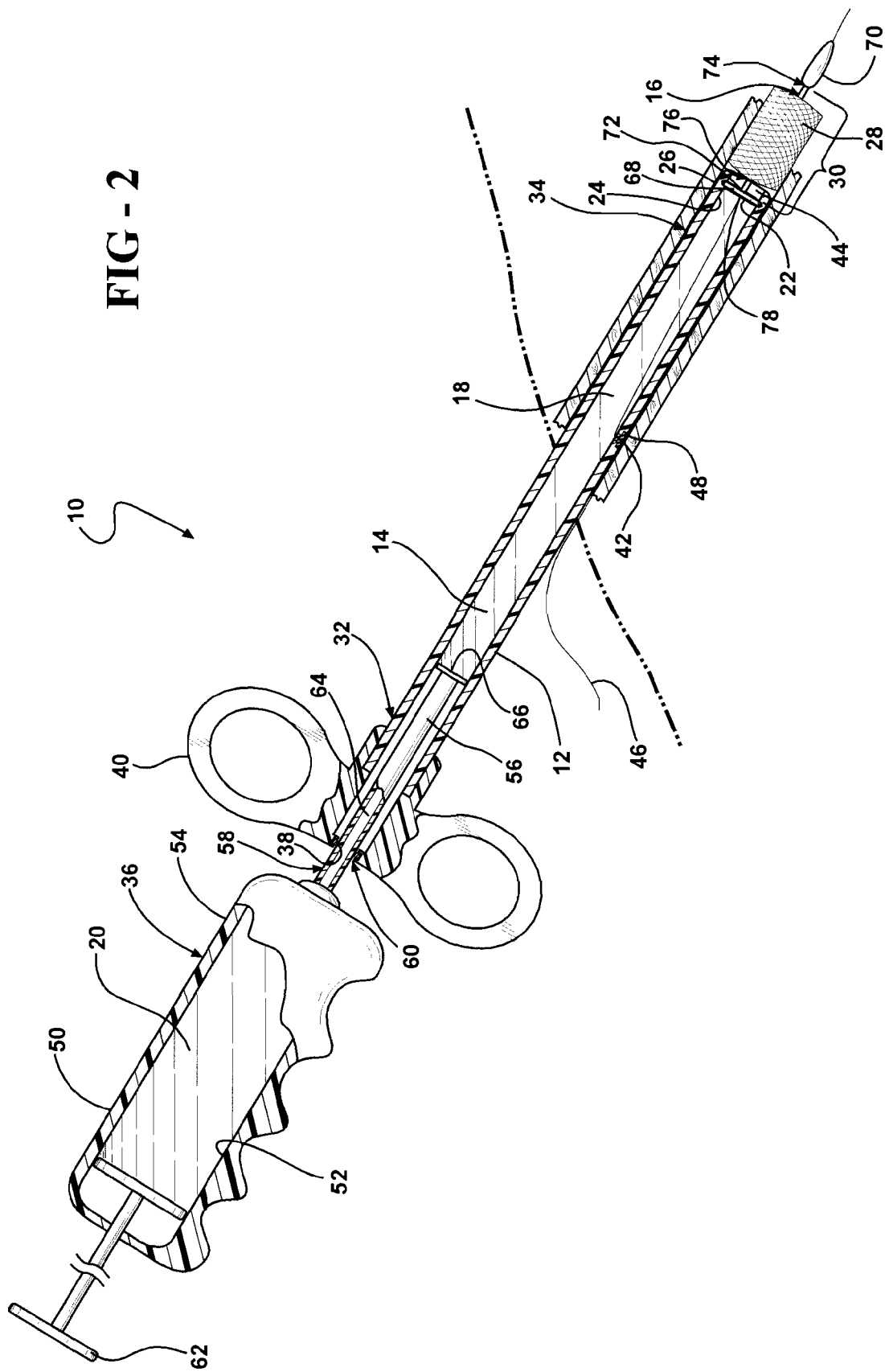
FIG. 2 is a sectional view of the delivery system illustrated in FIG. 1 partially disposed within a body vessel. The delivery system is shown in a stage of deployment with the self-expandable intraluminal medical device fully deployed.

FIGS. 1 and 2 illustrate a delivery system 10 according to a first exemplary embodiment. Delivery system 10 comprises a sheath member 12 defining a first passageway 14, an inner member 16 slidably disposed within a distal cavity 18 of the first passageway 14 of the sheath member 12, a fluid 20 that substantially prevents movement of the inner member 16 within the distal cavity 18 of the sheath member 12, and a groove 22 on a first inner surface 24 of the sheath member 12. A self-expandable intraluminal medical device 28 is disposed on a mounting region 30 of the inner member 16. The groove 22 prevents the inner member 16 from completely exiting the sheath member 12.

The entire delivery system 10 can be advanced over a wire guide 46 to navigate in a body vessel and to a point of treatment for the deployment of the self-expandable intraluminal medical device 28. The use of wireguides in the placement of delivery systems and intraluminal medical devices within body vessels is well known in the art and will not be described in detail herein.

The sheath member 12 can be any suitable tubular member, such as a sheath formed of plastic or other suitable material. Other examples of suitable tubular members include introducers, guiding catheters, and endoscopes. The sheath member 12 has the first inner surface 24 and a first outer surface 26 and defines the first passageway 14 that extends between a first proximal end 32 and a first distal end 34. The first passageway 14 provides the distal cavity 18 within which other components of the delivery system 10 can be disposed. In the illustrated embodiment, the distal cavity 18 is a portion of and is continuous with the first passageway 14. It is understood that, while the sheath member 12 is illustrated with a constant inner diameter along its length, varying inner diameters can be used, including varying inner diameters that, in effect, at least partially separate the distal cavity 18 from the remainder of the first passageway 14.

A reservoir unit 36 that contains a fluid 20 is slidably disposed within the first proximal end 32 of the sheath member 12. The reservoir unit 36 is discussed in further detail below. The first proximal end 32 of the sheath member 12 also comprises a first seal 38 that prevents the fluid 20 from escaping the sheath member 12.

Also, a grip 40 is located on the first proximal end 32 on the outer surface 26 of the sheath member 12. The grip 40 can be any suitable configuration that allows the user to grasp the sheath member 12 and retract it proximally away from the point of treatment. Further, the grip 40 can be integrally formed with the sheath member 12 or separately formed and attached. As illustrated by FIGS. 1 and 2, the grip 40 can form finger holes. The grip 40 could also be undulations ergonomically designed to be grasped by the user. The grip could also be a portion of the sheath member 12 with a different surface or texture to be grasped by the user. These elements, however, are not required and the sheath member 12 can indeed comprise a simple tubular body so long as the user is able to retract the sheath member 12 as necessary to operate the system.

The sheath member 12 in the illustrated embodiment is adapted for use in short-wire based devices and techniques, such as rapid exchange and remote uncoupling devices and techniques, which are adapted to allow the use of relatively short wireguides as compared to those used in standard over-the-wire devices and techniques. It is understood, though, that the invention can be utilized in both standard over-the-wire and short wire devices and techniques, including rapid exchange and remote-uncoupling based devices and techniques. In the illustrated embodiment, the sheath member 12 defines an exchange port 42 in its circumferential wall. The exchange port 42 comprises an opening that provides access from the external environment into the first passageway 14 of the sheath member 12 and a second seal 48 that prevents the fluid 20 from escaping the sheath member 12 during rapid exchange applications. The portion of the first passageway 14 extending between the exchange port 42 and the opening 44 at the first distal end 34 of the sheath member 12 provides a wire guide lumen that spans only a portion of the length of the sheath member 12. In use, a wireguide 46 passes through the opening 44 at the first distal end 34 of the sheath member 12, through the inner member 16, into the first passageway 14, and exits the sheath member 12 through the exchange port 42. The inner member 16, as described in more detail below, advantageously defines a wireguide lumen to facilitate this arrangement of a wireguide through the delivery system 10. This configuration facilitates use of the delivery system 10 in rapid exchange techniques.

As illustrated in FIGS. 1 and 2, the reservoir unit 36 is in fluid communication with the first passageway 14 at the first proximal end 32 of the sheath member 12. The reservoir unit 36 comprises a chamber 50 further comprising a second inner surface 52 and a second outer surface 54 and containing the fluid 20, a stem 56 with a second proximal end 58 and a second distal end 60, a flange 66, and a plunger 62. The stem 56 defines a second passageway 64 that extends between the second proximal 58 and distal ends 60.

The stem 56 is fixed to the distal end of the chamber 50. The stem 56 and chamber 50 may be integrally formed or formed separately and attached. The stem 56 is slidably disposed within the first passageway 14 at the first proximal end 32 of the sheath member 12. The flange 66 located at the second distal end of the stem 56 is advantageously designed to prevent the stem 56 from completely exiting the first passageway 14 of the sheath member 12. The first seal 38 on the first distal end 34 of the sheath member 12 interacts with the outside surface of the stem 56 to prevent fluid from escaping the first passageway 14 of the sheath member 12. As best illustrated in FIG. 1, the first seal can interact with the flange 66 to prevent the stem 56 from completely exiting the first passageway 14 of the sheath member 12.

The flange 66 may be configured to allow removal of the stem 56 of the reservoir unit 36 from the first passageway 14 of the sheath member 12. Also, there may be no flange 66 at all. Once the reservoir unit 36 has been removed from the sheath member 12, a device may be attached to the first proximal end 32 of the sheath member 12 to provide a vacuum to draw the inner member 16 back into the sheath member 12 once the self-expandable intraluminal medical device 28 has been delivered to the point of treatment 82. For example, the first proximal end 32 of the sheath member 12 could comprise a luer fitting adapted to connect with a syringe. The syringe could then be used to provide a vacuum within the sheath member 12 to withdraw the inner member 16 back into the sheath member 12.

The plunger 62 is slidably disposed within the chamber 50 of the reservoir unit 36. The plunger 62 is advantageously designed to contact the second inner surface 52 of the chamber 50 to create a seal to prevent the fluid 20 from leaking past the plunger 62. As the plunger 62 is depressed the fluid 20 is transferred into the stem 56 and further into the first passageway 14 of the sheath member 12 until the fluid 20 contacts the proximal flange 68 of the inner member 16. By depressing the plunger 62 and transferring the fluid 20 into the stem, a fluid column is created within the first passageway 14 that maintains a pressure on a proximal flange 68 of the inner member 16. The pressure exerted by the fluid column substantially prevents movement of the inner member 16 within the distal cavity 18 of the sheath member 12 as the sheath member 12 is retracted. This allows the intraluminal medical device 28 to be deployed substantially at a desired location in the body vessel after navigating the delivery system 10 to a part of the body vessel such that the intraluminal medical device 28 is positioned substantially at the desired location prior to deployment. In this manner, the delivery system 10 allows an intraluminal medical device 28 to be deployed substantially at the same location in a body vessel as the intraluminal medical device 28 is at once navigation through the vessel is completed. The plunger 62 does not return to its original position until withdrawn proximally by the user.

The fluid 20 can be any fluid that will depend on a number of factors: materials of construction of the delivery system 10, viscosity of the fluid, size of the delivery system 10, cost of the fluid, and others. The fluid 20 could be, but is not limited to, saline, water, air, a gel, or a highly viscous fluid. The delivery system 10 can be prepackaged with the fluid 20 in the reservoir unit 36 or the fluid 20 can be packaged separately. Furthermore, prior to or during the implantation procedure the first passageway 14 of the sheath member 12 could be filled with the fluid 20 to ensure the fluid column is in place and contacting the proximal flange 68 of the inner member 16. It is expected to be advantageous to fill the resevoir unit 36 and first passageway 14, to the proximal flange 68 of the inner member 16, completely with the fluid 20 at some point prior to use of the delivery system 10. This can be done at the time of manufacture, in the procedure room immediately prior to use, or at any suitable time in between these periods.

The inner surface 24 of the sheath member 12 defines the groove 22. The groove 22 is located proximally to the opening 44 at the first distal end 32 of the sheath member 12. The groove 22, discussed in more detail below, prevents the inner member 16 from completely exiting the sheath member 12 as it is pulled away from the point of treatment 82.

The first passageway 14 of the sheath member 12 includes a distal cavity 18 that receives the inner member 16. In the illustrated embodiment, the distal cavity 18 is a portion of and is continuous with the first passageway 14. It is understood that, while the sheath member 12 is illustrated with a constant inner diameter along its length, that varying inner diameters can be used, including varying inner diameters that, in effect, at least partially separate the distal cavity 18 from the remainder of the first passageway 14.

The inner member 16 provides a structure for carrying the self-expandable intraluminal medical device 28. The inner member 16 comprises a separate member from the sheath member 12 and is slidably disposed within the distal cavity 18 of the sheath member 12. The inner member 16 comprises the proximal flange 68, a distal tip 70, a third proximal end 72, a third distal end 74, and the mounting region 30. The inner member 16 defines a third passageway 76 that extends between the third proximal end 72 and the third distal end 74. A portion of the wireguide 46 passes through the distal tip 70 at the third distal end 74 into the third passageway 76 and exits the inner member 16 through the proximal flange 68. A third seal 78 located at the third proximal end 72 of the third passageway 76 allows the wireguide 46 to pass through the inner member 16 but prevents the fluid 20 from entering the third passageway 76 of the inner member 16 from the first passageway 14 of the sheath member 12. The distal tip 70, proximal flange 68, and mounting region 30 may be unitarily formed or separately formed and attached. In this embodiment, the proximal flange 68 and distal tip 70 are continuous with the mounting region 30 of the inner member 16.

The distal tip 70 is the distal-most portion of the inner member 16. The distal tip 70 advantageously includes a rounded or conical configuration at the third distal end 74 as it is the leading surface of the delivery system 10 during navigation through body vessels. The distal tip 70 is advantageously formed of a pliable material, such as an elastomeric material, that enables the distal tip 70 to safely maneuver through the body vessels.

The proximal flange 68 is the third proximal end 72 of the inner member 16. The proximal flange 68 advantageously comprises any configuration with a diameter large enough to contact the inner surface 24 of the sheath member 12 to create a seal and prevent the fluid 20 from passing the proximal flange 68, yet allowing the inner member 16 to slidably move within the distal cavity 18 of the first passageway 14. The proximal flange 68 is advantageously formed of a relatively rigid material such as a plastic or metal material that enables the proximal flange 68 to engage the groove 22 to prevent the inner member 16 from completely exiting the sheath member 12.

The mounting region 30 is formed of any suitable material, including plastics and metals. The mounting region 30 is of sufficient length to accommodate the self-expandable intraluminal medical device 28. Any suitable type of self-expandable prosthetic device can be used with the delivery systems according to the invention, including self-expandable stents, prosthetic valves that include a self-expandable support frame, such as prosthetic valves for implantation in a vein (prosthetic venous valves), self-expandable filters, distal protection devices, vessel occluders, and other self-expandable devices. Suitable self-expandable medical devices for use with delivery systems according to the invention include those described in U.S. Pat. No. 6,200,336 to Pavcnik et al. for a MULTIPLE-SIDED INTRALUMINAL MEDICAL DEVICE; U.S. application for patent Ser. No. 10/642,372 of Pavcnik et al. for an IMPLANTABLE VASCULAR DEVICE, filed on Aug. 15, 2003; and U.S. application for patent Ser. No. 10/828,716 of Case, et al. for an ARTIFICIAL VALVE PROSTHESIS WITH IMPROVED FLOW DYNAMICS, filed on Apr. 21, 2004; the entire disclosures of which are hereby incorporated into this disclosure for the purpose of describing suitable self-expandable intraluminal medical devices for use with delivery systems described herein.

The groove 22 on the first inner surface 24 of the sheath member 12 is configured to engage the proximal flange 68 of the inner member 16. The groove 22 is configured such that the inner member 16 can be advanced out of the first passageway 14 of the sheath member 12 until the proximal flange 68 of the inner member 16 engages the groove. Engagement of the proximal flange 68 with the groove 22 provides sufficient impedance to prevent the inner member 16 from exiting the passageway 14 of the sheath member 12 as the sheath member 12 is retracted.

The groove 22 can be any suitable configuration that prevents the inner member 16 from exiting the passageway 14 of the sheath member 12 as the sheath member 12 is retracted. Suitable configurations of the groove 22 include, but are not limited to, a protrusion, a circumferential intermittent groove, or a continuous circumferential groove. The embodiment illustrated in FIGS. 1 and 2 shows a continuous circumferential groove configuration. The proximal flange 68 is designed to fit into the groove 22 to prevent the inner member 16 from exiting the passageway 14 of the sheath member 12 as the sheath member 12 is retracted. To facilitate engagement of a recessed groove, the proximal flange 68 can be advantageously formed of a relatively rigid flexible material and can be slightly oversized with respect to the inner diameter of the first passageway 14.

The delivery system 10 can be operated in the following manner. First, the wireguide 46 is navigated through a body vessel 80 to the point of treatment 82 at which deployment of the self-expandable intraluminal medical device 28 is desired. Once the wireguide 46 is in an appropriate position, the delivery system 10 is navigated over the previously placed wireguide 46.

Once in proper position, the inner member 16 is deployed by proximally retracting the sheath member 12 to expose the inner member 16. The fluid 20 is advantageously used to maintain the axial position of the inner member 16. As the sheath member 12 is retracted the plunger 62 is depressed to transfer the fluid 20 from the reservoir unit 36 to the first passageway 14 of the sheath member 12. The infusion of the fluid 20 into the sheath member 12 compensates for the increase in volume within the first passageway 14 of the sheath member 12 to provide additional fluid in proportion to the volume being added by retracting the sheath member 12 so that the fluid column neither advances nor retracts the inner member 16.

With the first passageway 14 of the sheath member filled by the fluid 20 to substantially prevent axial movement of the inner member 16, the sheath member 12 is retracted. Retraction of the sheath member 12 is continued until the proximal flange 68 of the inner member 16 engages the groove 22 on the first inner surface 24 of the sheath member. Once this engagement has occurred, the mounting region 30 of the inner member 16 will be outside the delivery system 10. At this point, the self-expandable intraluminal medical device 28 is fully deployed.

Once the self-expandable intraluminal medical device 28 is fully deployed the inner member 16 can be retracted into the sheath member 12 by pulling back on the plunger 62. In a luer fitting and syringe embodiment, the syringe would be withdrawn to pull the inner member 16 back into the sheath member 12. In an embodiment that includes a removable reservoir unit 36, the reservoir unit 36 could be removed and a means for applying a vacuum force, such as a syringe, tubing connected to a pump, a pump, and other suitable means, could be attached to the sheath member 12 to facilitate the retraction of the inner member 16. Once the inner member 16 is retracted proximally into the sheath member 12, the delivery system 10 can be retracted along the wire guide 30 and ultimately removed from the body vessel 80, leaving the self-expandable intraluminal medical device 28 at the point of treatment 82.

Another exemplary embodiment of the invention (not illustrated) is similar to the embodiment illustrated in FIGS. 1 and 2 except that the reservoir unit does not contain a plunger. The reservoir unit is advantageously designed and constructed such that a user could squeeze the reservoir unit to transfer the fluid into the sheath member to contact the inner member. Adequate one-way and two-way seals or valves within the system would ensure this embodiment functions similarly to the embodiment illustrated in FIGS. 1 and 2.

Figure 3:
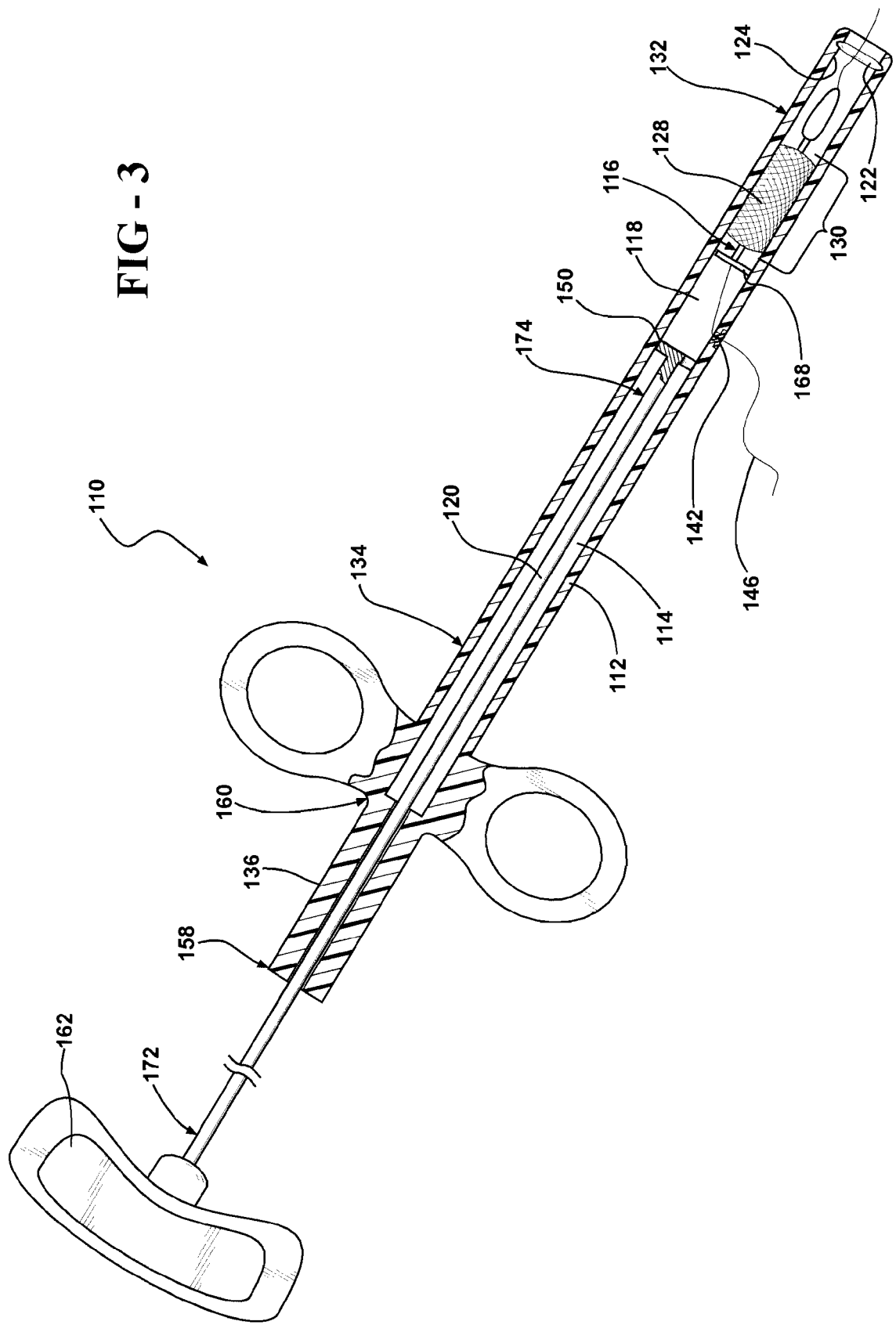
FIG. 3 is a sectional view of a delivery system according to a second exemplary embodiment.

FIG. 3 illustrates a delivery system 110 according to a second exemplary embodiment. The delivery system 110 according to this embodiment is similar to the delivery system illustrated in FIGS. 1 and 2 except as described below.

Delivery system 110 comprises a sheath member 112 defining a first passageway 114, a proximal tubular member 136, an inner member 116 slidably disposed within a distal cavity 118 of the first passageway 114 of the sheath member 112, a pusher 128 that substantially prevents movement of the inner member 116 within the distal cavity 118 of the sheath member 112, and a groove 122 on a first inner surface 124 of the sheath member. A self-expandable intraluminal medical device 128 is disposed on a mounting region 130 of the inner member 116, as best illustrated in FIG. 3.

As illustrated in FIG. 3, the proximal tubular member 136 is located at a first proximal end 132 of the sheath member 112. The proximal tubular member 136 comprises a second proximal end 158, a second distal end 160, and a second passageway 164 defined by the second proximal 158 and distal 160 ends. The proximal tubular member 126 may be may be integrally formed with the sheath member 112 or formed separately and attached. The embodiment illustrated in FIG. 3 shows a proximal tubular member 126 formed separately from and attached to the sheath member 112.

The pusher 120 is slidably disposed within the proximal tubular member 136 and the sheath member 112. The pusher 120 comprises a third proximal end 172, a third distal end 174, and a distal flange 150, and a proximal handle 162. The pusher 120 is moved and positioned using the proximal handle 162. The pusher 120 is moved into a position such that the distal flange 150 abuts a proximal flange 168 of the inner member 116. The pusher 120 substantially prevents axial movement of the inner member 116 within the distal cavity 118 of the sheath member 112. The second proximal end 158 of the proximal tubular member 136 may be advantageously designed to interact with the pusher 118 so that it does not move during retraction of the sheath member 112. The second proximal end 158 of the proximal tubular member 136 may involve a snap, screw, velcro, or adhesive to prevent axial movement of the pusher 120. The pusher 120 is advantageously formed of a relatively stiff material, such as a wire rod or hardened plastic. Also, hardened plastic including a wire core could be used.

The distal flange 150 of the pusher 120 is adapted to allow a portion of a wireguide 146 to pass the pusher 120 to exit the delivery system 110 through an exchange port 142. The distal flange 150 could be a semi-circular configuration as illustrated in FIG. 3, comprise an angled or indented portion, or any other suitable configuration that allows a portion of a wireguide 146 to pass the pusher 120 to exit the delivery system 110 through the exchange port 142.

The delivery system 110 can be operated in the following manner. First, the wireguide 146 is navigated through a body vessel to a point of treatment at which deployment of the self-expandable intraluminal medical device 128 is desired. Once the wireguide 146 is in an appropriate position, the delivery system 110 is navigated over the previously placed wireguide 146.

The pusher 120 is then moved into position using the proximal handle 162 such that the distal flange 150 abuts the proximal flange 168 of the inner member 116. The pusher 120 advantageously maintains the axial position of the inner member 116 during retraction. With the pusher 120 in position to substantially prevent axial movement of the inner member 116, the sheath member 112 is retracted. Retraction of the sheath member 112 is continued until the proximal flange 68 of the inner member 116 engages the surface groove 22 on the inner first surface 24 of the sheath member. Once this engagement has occurred, the mounting region 130 of the inner member 116 will be outside the delivery system 110. At this point, the self-expandable intraluminal medical device 28 is fully deployed.

Once the self-expandable intraluminal medical device 128 is fully deployed the inner member 116 can be retracted into the sheath member 112. Removal of the inner member 116 can be accomplished by removing the pusher 120 and attaching a vacuum to the delivery system 110 or the pusher 120 could be advantageously designed to connect with the proximal flange 168 of the inner member 116 and the pusher 120 pulled back to withdraw the inner member 116 into the sheath member 112. Once the inner member 116 is retracted back into the sheath member 112, the delivery system 110 can be retracted along the wire guide 146 and ultimately removed from the body vessel, leaving the self-expandable intraluminal medical device 128 at the point of treatment.

The foregoing disclosure includes the best mode of the inventor for practicing the invention. It is apparent, however, that those skilled in the relevant art will recognize variations of the invention that are not described herein. While the invention is defined by the appended claims, the invention is not limited to the literal meaning of the claims. Rather, it is expressly contemplated that the invention encompasses these and all other variations permitted by relevant law.

I claim:

1. A delivery system for placing a medical device within a body vessel, said delivery system comprising:

a sheath member having a sheath member proximal end, a sheath member distal end, a circumferential wall, an inner surface, and an outer surface, the sheath member defining a first passageway having a first passageway proximal end and a first passageway distal end, the first passageway extending between the sheath member proximal and sheath member distal ends and having a distal cavity located within the first passageway and axially spaced from the sheath member proximal end, the circumferential wall defining an opening providing access from the environment external to the sheath member to the first passageway;

an inner member having an inner member distal end comprising a distal tip, an inner member proximal end comprising a proximal flange, and a mounting region about which said medical device can be disposed, the inner member defining a second passageway extending between the distal tip and proximal flange and being slidably disposed within the distal cavity such that the inner member proximal end is disposed within the distal cavity, the inner member movable between a first position in which the inner member is disposed entirely within the first passageway and a second position in which the inner member is partially disposed within the first passageway and partially disposed outside the first passageway; and a fluid disposed in the first passageway and in contact with the proximal flange;

wherein only the fluid is disposed within an axial portion of the first passageway extending between the first passageway proximal end and the opening in the circumferential wall;

wherein the inner surface of the sheath member defines a groove adapted to temporarily engage the proximal flange of the inner member.

2. A delivery system according to claim 1, further comprising a reservoir defining a chamber in fluid communication with the first passageway, the chamber adapted to receive at least a portion of the fluid.

3. A delivery system according to claim 2, wherein the reservoir comprises a stem comprising a stem proximal end, a stem distal end, and defining a third passageway extending between the stem proximal and stem distal ends, the stem distal end slidably disposed within the first passageway of the sheath member.

4. A delivery system according to claim 3, wherein the reservoir is integrally formed with the stem.

5. A delivery system according to claim 3, wherein the reservoir comprises a separate member attached to the stem.

6. A delivery system according to claim 2, further comprising a plunger adapted to force a portion of the fluid from the chamber into the first passageway.

7. A delivery system according to claim 1, wherein the groove comprises a continuous circumferential groove.

8. A delivery system according to claim 1, wherein the first passageway has an inner diameter; and wherein the proximal flange is slightly oversized with respect to the inner diameter.

9. A delivery system for placing a medical device within a body vessel, said delivery system comprising:

a sheath member having a sheath member proximal end, a sheath member distal end, a circumferential wall, an inner surface, and an outer surface, the sheath member defining a first passageway having a first passageway proximal end and a first passageway distal end, the first passageway extending between the sheath member proximal and sheath member distal ends and having a distal cavity located within the first passageway and axially spaced from the sheath member proximal end, the circumferential wall defining an opening providing access from the environment external to the sheath member to the first passageway;

an inner member having an inner member distal end comprising a distal tip, an inner member proximal end comprising a proximal flange, and a mounting region about which said medical device can be disposed, the inner member defining a second passageway extending between the distal tip and proximal flange and being slidably disposed within the distal cavity such that the inner member proximal end is disposed within the distal cavity, the inner member movable between a first position in which the inner member is disposed entirely within the first passageway and a second position in which the inner member is partially disposed within the first passageway and partially disposed outside the first passageway;

a reservoir disposed on the proximal end of the sheath member and defining a chamber in fluid communication with the first passageway;

a fluid disposed in the first passageway and in contact with the proximal flange; and a plunger associated with the reservoir and adapted to force a portion of the fluid from the chamber and into the first passageway;

wherein only the fluid is disposed within an axial portion of the first passageway extending between the first passageway proximal end and the opening in the circumferential wall;

wherein the inner surface of the sheath member defines a groove adapted to temporarily engage the proximal flange of the inner member.

10. A delivery system according to claim 9, wherein the reservoir comprises an exterior surface that defines structural adaptations that form a grip for grasping the reservoir by a user of said delivery system.

11. A delivery system according to claim 9, wherein the reservoir comprises a stem, the stem defining a third passageway extending between the chamber and the first passageway of the sheath member and providing fluid communication between the chamber and the first passageway.

12. A delivery system according to claim 11, wherein the reservoir is integrally formed with the stem.

13. A delivery system according to claim 11, wherein the reservoir comprises a separate member attached to the stem.

14. A delivery system according to claim 11, wherein the stem comprises a distal flange having a circumferential surface in continuous contact with the inner surface of the sheath member.

15. A delivery system according to claim 9, further comprising a grip disposed on the proximal end of the sheath member.

16. A delivery system according to claim 15, wherein the grip comprises at least one ring defining a hole capable of receiving a finger of a user of said delivery system therethrough.

17. A delivery system for placing a medical device within a body vessel, said delivery system comprising:

a sheath member having a sheath member proximal end, a sheath member distal end, a circumferential wall, an inner surface, and an outer surface, the sheath member defining a first passageway having a first passageway proximal end and a first passageway distal end, the first passageway extending between the sheath member proximal and sheath member distal ends and having a distal cavity, the circumferential wall defining an opening providing access from the environment external to the sheath member to the first passageway;

an inner member having a distal tip, a proximal flange, and a mounting region about which said medical device can be disposed, the inner member defining a second passageway extending between the distal tip and proximal flange and being slidably disposed within the distal cavity, the inner member movable between a first position in which the inner member is disposed entirely within the first passageway and a second position in which the inner member is partially disposed within the first passageway and partially disposed outside the first passageway;

a reservoir disposed on the proximal end of the sheath member and defining a chamber in fluid communication with the first passageway, the reservoir including a stem defining a third passageway extending between the chamber and the first passageway of the sheath member and providing fluid communication between the chamber and the first passageway;

a fluid disposed in the first passageway and in contact with the proximal flange; a plunger associated with the reservoir and adapted to force a portion of the fluid from the chamber and into the first passageway; and a grip disposed on the proximal end of the sheath member; wherein the inner surface of the sheath member defines a groove adapted to temporarily engage the proximal flange of the inner member; and wherein only the fluid and the stem are disposed within an axial portion of the first passageway extending between the first passageway proximal end and the opening in the circumferential wall.

18. A delivery system according to claim 17, wherein the grip comprises at least one ring defining a hole capable of receiving a finger of a user of said delivery system therethrough.

* * * * *